United States Patent [19]

Olofson et al.

[11] Patent Number: 5,283,358
[45] Date of Patent: Feb. 1, 1994

[54] PROCESS FOR OBTAINING ARYL ESTERS BY O-DEALKYLATION AND APPLICATIONS

[75] Inventors: Roy A. Olofson, State College, Pa.; Ann P. Lawson, Lancashire, Del.; Heather L. Rayle, Los Angeles, Calif.

[73] Assignee: Societe Nationale des Poudres et Explosifs, Paris, France

[21] Appl. No.: 988,870

[22] Filed: Dec. 10, 1992

[30] Foreign Application Priority Data

Dec. 13, 1991 [FR] France .................. 91 15548

[51] Int. Cl.⁵ .............................................. C07C 69/76
[52] U.S. Cl. .................................................... 560/106
[58] Field of Search ................................ 560/106, 107

[56] References Cited

U.S. PATENT DOCUMENTS 4,835,304  5/1989  Williams .................. 560/106 X

FOREIGN PATENT DOCUMENTS

WO89/10913  11/1989  PCT Int'l Appl. .

Primary Examiner—Arthur C. Prescott
Attorney, Agent, or Firm—Jacobson, Price, Holman & Stern

[57] ABSTRACT

Process for obtaining aryl esters by O-dealkylation of an alkyl aryl ether with an acyl halide in the presence of a catalyst chosen from hexaalkylguanidinium salts and tetraalkylphosphonium salts.

The alkyl aryl ether corresponds preferentially to the formula $Ar(OR)_n$ in which R denotes an alkyl group, in particular a methyl group, n is an integer from 1 to 6 and Ar represents a $C_6$ to $C_{14}$ aromatic radical, a coumarinyl group or a group of a number of phenyl radicals.

This process allows also the obtention of aromatic polyester.

19 Claims, No Drawings

PROCESS FOR OBTAINING ARYL ESTERS BY O-DEALKYLATION AND APPLICATIONS

FIELD OF THE INVENTION

The present invention relates to a new process for obtaining aryl esters by O-dealkylation of an alkyl aryl ether in the presence of catalyst.

DESCRIPTION OF THE PRIOR ART

Many chemical operations performed on compounds bearing hydroxyl groups on aromatic rings require their O-protection beforehand to avoid undesirable reactions [T. W. Greene, Protective groups in organic synthesis, John Wiley, New York, 1981, 89–92 and Houben-Weyl, Methoden der organischen Chemie, Georg Thieme Verlag, 1976, Volume 6, Part 1C, p.313]. Indeed, aromatic hydroxyl functional groups can react with many reactants such as electrophilic ones, oxidizing agents and even alkylating or acylating agents.

Alkylation, and more precisely the methylation of phenolic hydroxyl groups which results in methyl aryl ethers, is a method of protection which is particularly useful because of the stability of the alkoxy groups.

Unfortunately, the final liberation of the phenolic hydroxyl functional groups of methyl aryl esters is always found to be difficult and requires severe conditions or very costly reactants.

Among the most commonly employed cleaving reactants there may be mentioned:

hydrogen halide acids (HBr, HI) [Greene (1981), op. cit., p.89]. In this, oldest method, introduced by Zeisel [Monatsh. Chem. (1885) 6, 989 and (1886) 7, 406], the substrate is heated to reflux with the hydrogen halide acid. The reaction conditions are so severe that most of the substituents of aromatic nuclei are destroyed;

pyridinium hydrochloride [R. Royer and P. Demerseman, Bull. Soc. Chim. France (1968) 2633]. In this case the substrate is heated to 200°–220° C. with at least 3 equivalents of pyridinium hydrochloride. The results are highly dependent on small changes in the operating conditions [J. P. Pepe, Ph.D. theesis, The Pennsylvania State University (1976) page 84]. Moreover, a number of types of interfering reactions are possible, including especially migrations of methyl groups [J. H. P. Tyman, J. Chem. Soc. Chem. Comm. (1972) 914];

boron tribromide and trichloride. BBr$_3$ is at present the reactant most widely employed for the non-selective O-demethylation of methyl aryl ethers [McOmie et al., Tetrahedron (1968) 24, 2289]. However, it also cleaves esters [A. M. Felix, J. Org. Chem. (1974) 39, 1427] and acetals [M. W. Bhatt and S. V. Kuskarni, Synthesis (1983) 249]. In addition, interfering reactions take place in the presence of ketone groups [J. T. Martz, Ph.D. thesis, The Pennsylvania State University (1982) p.26] and aldehyde groups [J. M. Lansinger and R. C. Ronald, Synth. Comm.(1979) 9, 341].

Other cleaving agents have been proposed. All of them exhibit, in various degrees, serious disadvantages, for example:

Me$_3$SiI and Ph$_2$PLi, which are very costly reactants,
EtSNa, which is a contaminating reactant, and
NaCN/DMSO, which is a highly toxic reactant.

Me, Et and Ph are the abbreviations for methyl, ethyl and phenyl radicals respectively, and DMSO is the abbreviation for dimethyl sulfoxide.

Thus, none of the numerous methods of O-demethylation which are described in the prior art gives fully satisfactory results, as illustrated by J. R. Hwu and S. C. Tsay [J. Org. Chem. (1990) 55, 5987–91]. These authors also introduce a new cleaving reactant, Me$_3$SiSNa, which, although yielding advantageous results, is confined to the laboratory because of its cost and contamination problems.

Esterification of phenolic compounds also presents many problems [Houben-Weyl, Methoden der organischen Chemie, George Thieme Verlag 1985, Volume E5 Part 1, p. 697].

Indeed, phenols are sensitive to oxidation in alkaline media, and the esters obtained therein are partially hydrolyzed, and this makes it tricky to work in a basic medium in order to carry out the condensation of an acid chloride with a phenol according to the following reaction:

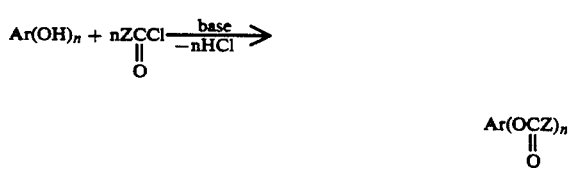

Despite its disadvantages, this method is in practice the only one employed.

It should be noted, furthermore, that the literature contains hardly any descriptions of the preparation of aryl esters by reaction of an alkyl aryl ether with an acid chloride. In only one, very old, publication (V. Prey, Chem. Ber. 75 B, No. 5, 1942, p. 544) anisole and veratrole were reacted with benzoyl chloride. Anisole does not react. In the case of veratrole, a mixture of 2-methoxyphenol and of pyrocatecol was apparently obtained. However, this result could not be reproduced.

In the prior art there is therefore no known method for protecting the hydroxyl functional group of phenolic compounds in an effective, stable but easily reversible manner.

The protection of hydroxyl functional groups by forming alkyl aryl ethers is difficult to reverse, while alkyl aryl esters are too unstable in basic medium.

GENERAL DESCRIPTION OF THE INVENTION

According to the invention, it has been surprisingly found that it is possible, in particular catalytic conditions, to form aryl esters from alkyl aryl ethers.

The inventors have thus shown that it is possible to protect the hydroxyl groups of phenolic nuclei in a simple, reliable and reversible manner.

The inventors have thus established that it is possible to synthesize aromatic polyesters in this manner.

The subject of the present invention is therefore a process for obtaining an aryl ester by O-dealkylation of an alkyl aryl ether, wherein an alkyl aryl ether is reacted with an acyl halide in the presence of a catalyst chosen from hexaalkylguanidinium salts and tetraalkylphosphonium salts.

Advantageously, guanidinium salts correspond to the formula:

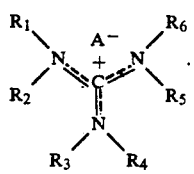

and phosphonium salts to the formula:

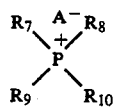

in which formulae $R_1$ to $R_{10}$ are identical or different and denote $C_1$-$C_{20}$ alkyl radicals and $A^-$ denotes an anion chosen from the group comprising $Cl^-$, $Br^-$, $I^-$, $BF_4^-$, $CN^-$, $ClO_4^-$ $NO_3^-$, $NO_2^-$, $OCN^-$, $CH_3SO_4^-$ and $HSO_4^-$.

The radicals $R_7$ to $R_{10}$ preferably contain from 4 to 18 carbon atoms.

According to a preferred alternative form, the process according to the invention is applicable to alkyl aryl ethers of formula $Ar(OR)_n$ in which:

R denotes a primary or secondary $C_1$-$C_6$ alkyl group, in particular a methyl group, n is an integer from 1 to 6 and Ar denotes:

a $C_6$-$C_{14}$ aromatic radical, preferably phenyl or naphthyl, optionally substituted by one or more, identical or different groups such as halogen atoms, in particular F, Cl, Br, nitro, cyano or aldehyde groups, alkoxy, aryloxy or substituted aryloxy groups, for example alkylaryloxy or haloalkylaryloxy groups, aryl-, alkyl- or cycloalkylketone groups, aryl groups, in particular phenyl, or $C_1$-$C_{20}$ alkyl groups, branched or unbranched, substituted or unsubstituted, for example by a phenyl group, the coumarinyl group or a group of a number of phenyl radicals, it being possible for each phenyl radical to carry one or more OR groups, in particular $Ar(OR)_n$ may denote radicals of formula:

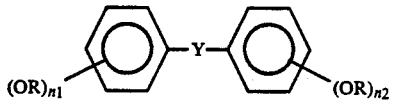

in which Y denotes

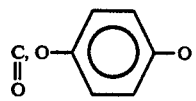

or a covalent bond, and $n_1$, $n_2$ are identical or different integers from 1 to 3.

When a number of radicals R are present in the compound, these radicals may be identical or different.

The acyl halide which is reacted with the alkyl aryl ether may be denoted by the general formula

in which:

X denotes a halogen, in particular Br or Cl,

Z denotes a $C_6$-$C_{10}$ aromatic radical, preferably the phenyl radical, optionally substituted by radicals chosen from alkyl radicals, halogen atoms and phenoxy radicals, an aliphatic or cycloaliphatic radical with up to 20 carbon atoms, preferably with 6 to 20 carbon atoms, saturated or unsaturated, substituted or unsubstituted, for example by a phenyl group, a phenoxy radical, it being possible for said radicals also to contain or be substituted by another

group. In this case, a polyester can be obtained by reaction with the alkyl aryl ether $Ar(OR)_n$ with $n \geq 2$.

When n=1 the reaction scheme is written as follows:

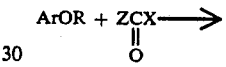

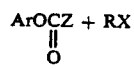

The hexaalkylguanidinium salts employed as catalysts in the process according to the invention are known compounds, which can be prepared by the processes described in Patent FR No. 2,585,351. The radicals $R_1$ to $R_6$ preferably have from 1 to 5 carbon atoms. The anion is generally a halide, advantageously a chloride, which may be in hydrochloride form.

Catalysts which are particularly appropriate are hexabutylguanidinium or hexamethylguanidinium chlorides (HBGC or HMGC), employed as such or in hydrochloride form.

In the phosphonium salts, the radical $R_7$ to $R_{10}$ preferably contain from 4 to 18 carbon atoms. The anion is that which is the most easily available.

Suitable catalysts are, for example, tributylhexadecylphosphonium bromide and tetrabutylphosphonium bromide.

The reaction of O-dealkylation of alkyl aryl ethers, performed according to the invention, makes it possible to avoid the use of costly or contaminating reactants and prevents the modification or the removal of the other substituents of the aromatic nucleus.

The invention can be applied to the deprotection of aromatic —OH functional groups temporarily protected in the form of alkyl aryl ethers and, more precisely of methyl aryl ethers.

The aryl esters obtained by means of the process of the invention can be easily hydrolyzed in a basic medium, in particular using the classical method described in Houben-Weyl (Methoden der organischen Chemie, Georg Thieme Verlag, 1976, Volume 6, Part Ic, 436–451) to obtain phenols.

For this application, Z preferably denotes the phenyl radical.

As described by Greene (op. cit.), phenolic hydroxyl groups are present in many compounds of biological interest, such as tyrosine, thyroxine, estrone, codeine, terramycin, adrenalin and naloxone.

A stage of demethylation of a methyl aryl ether functional group may be involved in the synthesis of many other products such as, for example, pesticides. Thus, Patent DE 3,832,656 (cf. example 1) employs the demethylation of the compound

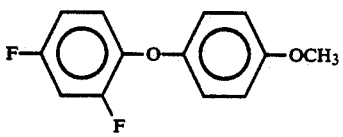

in the preparation of acaricides.

A second application of the invention is the synthesis of aromatic esters or polyesters. A large number of aryl benzoates are of great industrial interest, for example:

for the manufacture of liquid crystals [EP 99,488]

for reprography on heat-sensitive paper [U.S. Pat. No. 4,500,896]

for photosensitizers [DE 3,007,797]

for the stabilization of polymers [U.S. Pat. No. 4,110,301], for anti-UV absorbers [DE 3,417,782].

The process according to the invention can also be used for the preparation of polyesters which have very good thermal properties [J. Macromol. Sci. Chem. (1985) A 22 (5–7) p.561–577].

As a general rule, the invention can be applied under the following reaction conditions. From 0.01 to 0.1 equivalent of catalyst is advantageously employed per mole of —OR functional group to be cleaved. Catalysts which have been exposed to moisture must be dried before being employed.

Furthermore, the reaction temperature must be advantageously between 150° C. and 220° C. and preferably between 180° C. and 200° C.

From 1.0 to 3.0 equivalents of acyl halide functional group are generally employed per alkyl ether functional group to be cleaved, and, preferably 1.0 to 1.5 equivalents when n=1.

When possible, it is preferable to operate without solvent. In the case of alkyl aryl ethers which have high melting points (above 150° C.) or when it is desired to prepare polymers, it is possible to employ an inert solvent which preferably has a boiling point above 150° C., such as o-dichlorobenzene, 2,4-dichlorotoluene or 1,2,4-trichlorobenzene.

The reaction time is generally between 8 and 24 hours.

The present invention is illustrated by the following examples without, however, being limited thereby.

In these examples, the catalysts have been dried before use at 100° C. in vacuum for a few hours in the case of hexabutylguanidinium chloride (HBGC) or hexamethylguanidinium chloride (HMGC) or at 20° C. for 20 min in vacuum in the case of HBGC.HCl or HMGC.HCl.

EXAMPLE 1

O-Demethylation of p-anisonitrile to 4-cyanophenyl benzoate

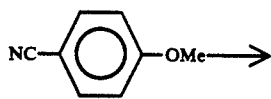

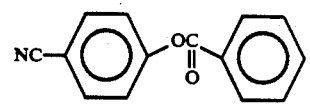

A) Catalysis by HBGC

A solution of 0.19 g (0.45 mmol; 0.04 eq.) of HBGC, 1.50 g (11.3 mmol) of anisonitrile and 1.60 g (11.4 mmol) of benzoyl chloride in 5 ml of o-dichlorobenzene(o-DCB) is stirred at 185° C. for 13 hours.

After distillation of the reaction medium under reduced pressure (80° C./1 mm Hg), the yellow solid residue is dissolved in 50 ml of CHCl$_3$ and stirred for 20 min with 1.5 g of silica. The silica which has adsorbed the catalyst is separated off by filtration. After removal of the solvent by evaporation under reduced pressure the expected product is purified by recrystallization from a CCl$_4$/hexane mixture. 3.26 g of white needles are obtained, that is a 96% yield.

The characteristics of the product are as follows:

Melting point (m.p.): 93°–94.5° C.

Ir(CHCl$_3$) $\vee$: 2180 (m), 1740 (s) cm$^{-1}$ $^1$H NMR (CDCl$_3$) δ: 8.21 (d of d, 2H, J=7-1 Hz); 7.8–7.65 (m, 3H); 7.6–7.5 (m,2H); 7.35 (d of d, 2H, J=8.5-2 Hz).

B. Catalysis by tributylhexadecylphosphonium bromide

A mixture of 1.73 g (13 mmol) of anisonitrile with 2.07 g (14.7 mmol) of benzoyl chloride and 0.33 g (0.65 mmol, 0.05 eq.) of tributylhexadecylphosphonium bromide is stirred at 185° C. for 16 hours. The brown solid obtained is then stirred with 3 g of silica in 75 ml of CH$_2$Cl$_2$. The mixture is filtered, the filtrate is concentrated and a solid is obtained which is recrystallized. 2.74 g of the expected product are isolated in the form of white needles (94% yield), m.p.: 93°–95° C.

C) Comparative test without catalyst

To demonstrate the role of the catalyst, test A was repeated with the same conditions but without adding catalyst.

Even after heating to 185° C. for 60 h the mixture obtained contains no trace of 4-cyanophenyl benzoate. The starting materials and a small quantity (<9%) of an unidentified impurity are collected.

EXAMPLE 2

Bis-(O-demethylation) of 4,4'-dimethoxybenzophenone

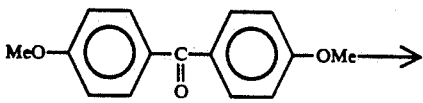

-continued

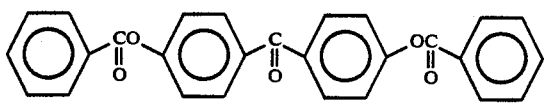

A mixture of 0.12 g (0.26 mmol) of HBGC.HCl, 1.04 g (4.29 mmol) of 4,4'-dimethoxybenzophenone and 1.85 g (13.2 mmol) of benzoyl chloride is stirred at 185° C. for 20 h.

After the removal of excess benzoyl chloride by distillation under reduced pressure the residue is treated with silica as indicated in example 1.

The product collected is washed with hexane and dried under vacuum. 1.73 g of a white powder are obtained (98% yield), which exhibits the following characteristics:

m.p.: 183.5°–184.5° C. IR (CHCl$_3$), 1740 (s), 1240 (s), 1140 (m) cm$^{-1}$, $^1$H NMR δ 8.3–8.2 (m,4H); 8.0–7.9 (m, 4H); 7.7–7.65 (m, 2H); 7.6–7.5 (m,4H), 7.4–7.35 (m,4H).

EXAMPLE 3

O-Demethylation of 2,4-dimethylanisole to 2,4-dimethylphenyl benzoate

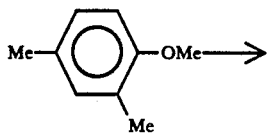

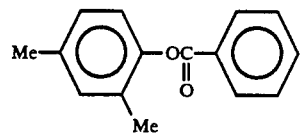

A) Catalysis by HBGC

A mixture of 0.21 g (0.44 ml) of HBGC.HCl, 1.54 g (11.3 mmol) of 2,4-dimethylanisole and 1.78 g (12.7 mmol) of benzoyl chloride is stirred at 185° C. for 19 hours. The crude mixture obtained is purified directly by thin-layer chromatography (22/75 v/v CH$_2$Cl$_2$/hexane, R$_f$ 0.28 ). 2.48 g (97% yield) of a viscous clear liquid are thus collected and this, on cooling to −10° C., gives white crystals (m.p.: 37°–39° C.) exhibiting the following characteristics:

IR(CCl$_4$) 1740 (s), 1240 (s), 1170 (s) cm$^{-1}$ $^1$H NMR (CDCl$_3$) δ 8.35–8.25 (m, 2H); 7.7–7.65 (m, 1H); 7.6–7.5 (m, 2H); 7.15–7.0 (m, 3H); 2.4 (s, 3H); 2.25 (s, 3H).

B) Catalysis by tetrabutylphosphonium bromide.

A mixture of 0.18 g (0.54 mmol, 0.10 eq) of tetrabutylphosphonium bromide, 0.76 g (5.58 mmol) of 2,4-dimethylanisole and 0.87 g (6.19 mmol) of benzoyl chloride is stirred at 185° C. for 20 hours. The crude yellow oil obtained is purified by chromatography (24/76 CH$_2$Cl$_2$/hexane). 1.13 g of the expected product (89% yield) are obtained.

C) Comparative test without catalyst

To demonstrate the role of the catalyst, test A was repeated without adding catalyst.

Even after heating to 185° C. for 60 hours, the mixture obtained contains no trace of 2,4-dimethyl-phenyl benzoate.

EXAMPLE 4

O-Demethylation of p-anisonitrile to 4-cyanophenyl 2-ethylhexanoate

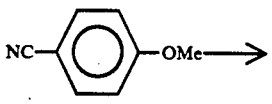

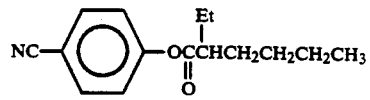

A solution of 0.18 g (0.41 mmol) of HBGC, 1.32 g (9.88 mmol) of p-anisonitrile and 1.67 g (10.1 mmol) of 2-ethylhexanoyl chloride in 4 ml of o-dichlorobenzene is stirred at 185° C. for 13 hours. After removal of the solvent by distillation under reduced pressure, the crude product obtained is purified by column chromatography (6 ethyl acetate/94 hexane; R$_f$=0.37).

2.36 g (98% yield) of the expected product are thus obtained in the form of a slightly yellow oil exhibiting the following characteristics:

Ir (CCl$_4$) 2180 (m) 1765 (s) cm$^{-1}$ $^1$H NMR (CDCl$_3$) δ 7.7–7.65 (m, 2H); 7.25–7.15 (m, 2H); 2.6–2.45 (m, 1H); 1.85–1.5 (m, 4H); 1.4–1.3 (m, 4H); 1.05–0.9 (m, 6H).

EXAMPLE 5

O-Debutylation of n-butyl phenyl ether to phenyl benzoate

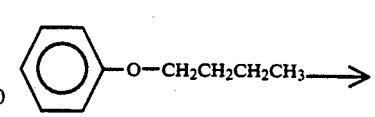

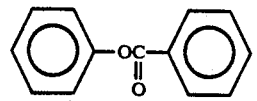

A mixture of 1.04 g (6.92 mmol) of n-butyl phenyl ether, 0.26 g (0.56 mmol) of HBGC.HCl and 1.21 g (8.61 mmol) of benzoyl chloride is stirred at 185° C. for 40 hours. The crude mixture obtained is purified by flash chromatography (35/65 CH$_2$Cl$_2$/hexane, R$_f$ 0.25).

1.29 g (94% yield) of the expected product are thus obtained in the form of a white crystalline product (m.p./ 68.5°–70° C.) exhibiting the following characteristics: IR(CDCl$_3$): 1730 (s), 1245 (s), 1180 (s) cm$^{-1}$ $^1$H NMR (CDCl$_3$) δ: 8.25–8.15 (m, 2H); 7.65–7.6 (m, 1H); 7.55–7.35 (m, 4H), 7.3–7.15 (m, 3H).

EXAMPLE 6

O-Demethylation of p-anisonitrile to 4-cyanophenyl palmitoate

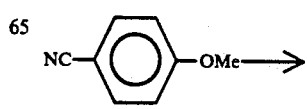

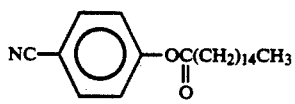

A mixture of 0.23 g (0.49 mmol) of HBGC.HCl, 1.65 g (12.4 mmol) of p-anisonitrile and 4.20 g (14.9 mmol) of palmitoyl chloride are stirred at 185° C. for 12 hours. After treatment with silica as indicated in example 1, the dark residue obtained is recrystallized twice from n-hexane.

4.13 g (93% yield) of the expected product are thus obtained in the form of white needles (M.p. 71°–74° C.) exhibiting the following characteristics:

IR (CDCl3): 2190 (m), 1765 (s), 1190 (s), 1145 cm$^{-1}$
$^1$H NMR (CDCl3) δ 7.7–7.65 (m, 2H); 7.25–7.2 (m, 2H); 2.58 (t, 2H, J=7.5 Hz); 1.85–1.7 (m, 2H); 1.45–1.2 (m, 24H); 0.88 (t, 3H, J=6.5 Hz).

EXAMPLE 7

O-Demethylation of p-anisonitrile to trans 4-cyanophenyl-cinnamate

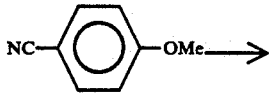

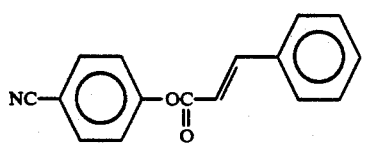

A mixture of 0.14 g (0.29 mmol) of HBGC.HCl, 0.97 g (7.29 mmol) of p-anisonitrile and 1.34 g (8.04 mmol) of trans-cinnamoyl chloride is stirred at 185° C. for 12 hours.

The volatile products are removed by distillation under reduced pressure and a treatment with silica is carried out as indicated in example 1.

The solid obtained is free from residual cinnamoyl chloride by washing with hexane and is recrystallized from the hexane/CCl4 mixture.

1.68 g (93% yield) of a white powder (M.p.104.5°–106° C.) are thus obtained, exhibiting the following characteristics:

IR (CDCl3): 2185 (m), 1730 (s), 1630 (s), 1190 (s), 1110 (s) cm$^{-1}$,
$^1$H NMR (CDCl3): δ 7.91 (d, 1H, J=16 Hz); 7.8–7.7 (m, 2H); 7.65–7.55 (m, 2H); 7.5–7.4 (m, 3H); 7.35–7.3 (m, 2H); 6.62 (d, 1H, J=16 Hz).

EXAMPLE 8

O-Demethylation of o-chloroanisole to 2-chlorophenyl benzoate.

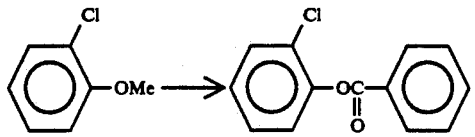

A heterogenous mixture of 0.12 g (0.57 mmol) of HMGC.HCl, 2.08 g (14.6 mmol) of 2-chloroanisole, 2.10 g (14.9 mmol) of benzoyl chloride and 3 ml of o-dichlorobenzene is stirred at 185° C. for 20 hours. After purification of the product by column chromatography (20/80 CH2/Cl2/hexane, R$_f$: 0.19), 2.49 g (73% yield) of the expected compound are obtained in the form of a slightly yellow liquid exhibiting the following characteristics:

IR (CCl4): 1750 (s), 1220 (s), 1195 (s), 1030 (s) cm$^{-1}$
$^1$H NMR (CDCl3): δ 8.3–8.2 (m, 2H); 7.75–7.6 (m, 1H); 7.6–7.5 (m, 3H); 7.4–7.2 (m, 3H).

EXAMPLE 9

O-Demethylation of p-anisonitrile to 4-cyanophenyl benzoate by employing benzoyl bromide.

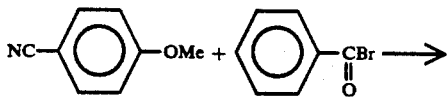

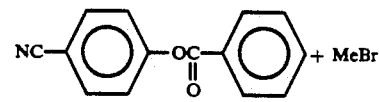

A mixture of 0.10 g (0.24 mmol) of HBGC, 0.79 g (5.93 mmol) of p-anisonitrile and 1.28 g (6.92 mmol) of benzoyl bromide is stirred at 185° C. until $^1$H NMR analysis shows the end of the reaction (4 hours).

The crude product obtained is dissolved in 75 ml of CHCl3, treated with 1.5 g of silica, filtered and concentrated. The solid obtained is redissolved in CHCl3, washed with 20 ml of an aqueous solution saturated with Na2CO3.

After removal of the solvent by distillation under reduced pressure and recrystallization from the hexane/CCl4 mixture, 1.25 g (95% yield) of the expected product are obtained, whose characteristics are the same as those given in example 1.

EXAMPLE 10

O-Demethylation of 2-methoxynaphtalene to 2-naphtyl benzoate

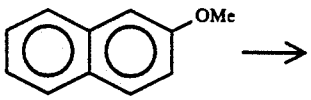

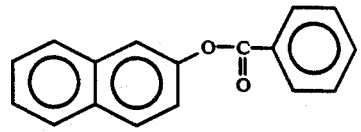

A mixture of 0.17 g (0.36 mmol) of HBGC,HCl, 1.47 g (9.29 mmol) of 2-methoxynaphtalene and 1.45 g (10.3 mmol) of benzoyl chloride is stirred at 185° C. for 20 hours. The solid obtained is dissolved in 75 ml of CH2Cl2 and the solution is treated with 3 g of silica.

After removal of the solvent by evaporation and purification by flash chromatography (26/74 CH2Cl2 in hexane, R$_f$: 0.19), 2.15 g (93% yield) of the expected product (M.p. 106.5°–107.5° C.) are obtained, exhibiting the following characteristics:

IR (CDCl3): 1735 (s), 1255 (s) cm$^{-1}$ $^1$H NMR (CDCl$_3$): δ 8.35-8.25 (m, 2H); 8.0-7.85 (m, 3H); 7.73 (d, 1H, J=2.2 Hz); 7.7-7.65 (m, 1H); 7.6-7.5 (m, 4H); 7.40 (d of d, 1H, J=8.9-2.3 Hz).

EXAMPLE 11

O-Demethylation of 4-methoxyphenyl 4'-trifluoromethylphenyl ether to 4-benzoyloxyphenyl 4'-trifluoromethylphenyl ether

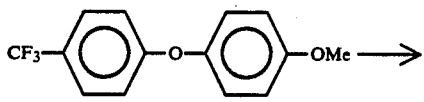

A mixture of 0.22 g (0.47 mmol) of HBGC.HCl, 2.53 g (9.43 mmol) of 4-methoxyphenyl 4'-trifluoromethylphenyl ether and 1.44 g (10.2 mmol) of benzoyl chloride is stirred at 185° C. for 18 hours.

After the removal of excess benzoyl chloride and treatment with silica as indicated in example 1, 3.38 g of a white solid are obtained in a purity higher than 99%.

Recrystallization from hexane gives 3.14 g (93% yield) of the expected product (M.p.: 95°-96° C.) which exhibits the following characteristics:

IR: (CCl$_4$)1735 (s), 1845 (s), 1310 (s), 1180 (s) cm$^{-1}$
$^1$H NMR (CDCl$_3$): δ 8.3-8.2 (m,2H); 7.7-7.45 (m, 5H); 7.3-7.2 (m, 2H); 7.15-7.0 -m, 4H).

EXAMPLE 12

O-Demethylation of 4-methoxystilbene to 4-benzoyloxystilbene.

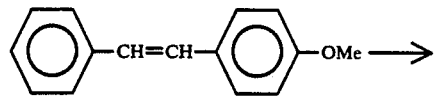

A mixture of 0.17 g (0.36 mmol) of HBGC.HCl, 1.49 g (7.09 mmol) of 4-methoxystilbene and 1.09 g (7.75 mmol) of benzoyl chloride is stirred at 185° C. for 15 hours. The orange-red solid obtained is ground with CCl$_4$ and filtered off. After recrystallization from toluene, 1.93 g (91% yield) of the expected product (M.p.: 195°-196° C.) are collected, exhibiting the following characteristics:

IR(KBr disk): 1730 (s), 1590 (w), 1490 (m), 1250 (s), 1180 (s) cm$^{-1}$
$^1$H NMR (CDC13): δ 8.3-8.2 (m) (m,2H); 7.7-7.5 (m,8H); 7.45-7.2 (m, 6H); 7.12 (s, 2H).

EXAMPLES 13 to 28

Monodemethylations of methyl aryl ethers carried out according to the procedure of example 1

The reaction is performed:
at 185° C. except in example 22, in which the reaction is performed at 160° C.,
with or without solvent,
in the presence of 0.04 eq. of catalyst.

The products obtained and the yields are shown in table I below for each of the ethers.

EXAMPLES 29 to 45

Poly(O-demethylations) of methyl aryl ethers carried out according to the procedure of example 2

The reaction is performed:
at 185° C.
with or without solvent.

Table II below shows the products obtained and the reaction yields.

EXAMPLES 46 to 53

Hydrolysis of benzoates obtained in the preceding examples with a view to liberating the hydroxyl functional group(s)

The operations are carried out at reflux in dioxane by treatment with an aqueous 3.8M sodium hydroxide solution under the following conditions:

dioxane: 100 ml per 20-25 g of ester
NaOH: 2 to 4 eq. per ester functional group to be hydrolyzed
reflux of the mixture: approximately 1 h.

After acidifying with concentrated hydrochloric acid, 1,000 ml of ether are added, the aqueous phase is washed with 500 ml of ether, and the combined ether phases are then washed with 250 ml of water and dried over MgSO$_4$.

After evaporation of the ether under reduced pressure, the solid is ground with 300 ml of chloroform. The insoluble product obtained is purified on a column (silica gel for flash chromatography, 40 μm), 30/70 ethyl acetate/hexane eluent.

The products obtained and the reaction yields are mentioned in table III below.

EXAMPLE 54

Preparation of a polymer by reaction of 4,4'-dimethoxybenzophenone with azelaoyl chloride

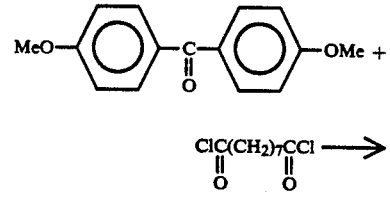

A mixture of 0.33 g (0.69 mmol) of HBGC.HCl, 2.1 g (8.60 mmol) of 4,4'-dimethoxybenzophenone, 1.935 g (8.60 mmol) of azelaoyl chloride and 5 ml of o-dichlorobenzene is stirred at 185° C. for 60 hours.

The mixture is then treated as indicated in example 1 (dissolution in 100 ml of CHCl$_3$), and the expected polymer is collected in the form of a powder by precipitation with hexane.

Molecular mass: approximately 39,000.

EXAMPLE 55

O-Demethylation of 1,2-dimethoxybenzene to 1,2-dibenzoyloxybenzene

A mixture of 0.15 g (0.03 eq., 0.35 mmol) of HBGC, 1.45 g (10.5 mmol) of veratrole (1,2-dimethoxybenzene) and 4.5 g (32 mmol) of benzoyl chloride was stirred at 185° C. for 46 hours. The excess reactants were distilled under vacuum and the catalyst was removed by absorption on silica from a solution in $CH_2Cl_2$. After evaporation of the solvent 3.32 g (99% crude yield) of a light brown solid are obtained. The pure product is isolated in the form of a white solid by cristallization from ethanol. Its characteristics are as follows:

M.p. 86°–87° C.

$^1$H NMR ($CDCl_3$) δ 8.05–8.1 (d, 4H), 7.5–7.6 (m, 2H), 7.3–7.45 (m, 8H).

IR ($CCl_4$) C=O line at 1750 $cm^{-1}$.

TABLE I

| Ex. | ETHER | Catalyst | Acid chloride ZCCl=O | Solvent | Time (h) | Product | Yield % |
|---|---|---|---|---|---|---|---|
| 13 | 4-NC-C6H4-OMe | MHGC | PhCCl=O | o-DCB | 22 | 4-NC-C6H4-OC(=O)Ph | 95 recrystallization |
| 14 | 4-NC-C6H4-OMe | HBGC | 3,5-Cl2-C6H3-CCl=O | o-DCB | 12 | 4-NC-C6H4-OC(=O)-C6H3-3,5-Cl2 | 86 recrystallization |
| 15 | 2,4-Me2-C6H3-OMe | HBGC | nC7H15CCl=O | none | 13 | 2,4-Me2-C6H3-OC(=O)-nC7H15 | 92 column chrom. |
| 16 | 2-Cl-C6H4-OMe | HBGC | PhCCl=O | none | 9 | 2-Cl-C6H4-OC(=O)Ph | 94 column chrom. |
| 17 | 7-MeO-coumarin | HBGC | PhCCl=O | o-DCB | 19 | 7-PhCO2-coumarin | 94 recrystallization |
| 18 | 7-MeO-coumarin | HBGC·HCl | PhCCl=O | none | 14 | 7-PhCO2-coumarin | 98 recrystallization |
| 19 | 4-Br-C6H4-OMe | HBGC | PhCCl=O | o-DCB | 19 | 4-Br-C6H4-OC(=O)Ph | 85 recrystallization |

TABLE I-continued

| Ex. | ETHER | Catalyst | Acid chloride ZCCl=O | Solvent | Time (h) | Product | Yield % |
|---|---|---|---|---|---|---|---|
| 20 | 4-Br-C6H4-OMe | HBGC.HCl | nC7H15CCl=O | none | 12 | 4-Br-C6H4-OC(=O)-nC7H15 | 95 column chrom. |
| 21 | 4-MeO-biphenyl | HBGC | PhCCl=O | none | 20 | 4-PhC(=O)O-biphenyl | 90 recrystallization |
| 22 | 3-F-C6H4-OMe | HBGC | PhCCl=O | none | 23 at 160° C. | 3-F-C6H4-OCPh=O | 74 column chrom. |
| 23 | 2,6-Me2-C6H3-OMe | HBGC.HCl | PhCCl=O | none | 20 | 2,6-Me2-C6H3-OCPh=O | 95 column chrom. |
| 24 | 4-OHC-C6H4-OMe | HBGC | PhCCl=O | o-DCB | 16 | 4-OHC-C6H4-OCPh=O | 62 recryst. |
| 25 | 2-MeO-naphthalene | HBGC.HCl | nC7H15CCl=O | none | 20 | 2-naphthyl-OC(=O)nC7H15 | 95 column chrom. |
| 26 | 4-NC-C6H4-OMe | HBGC.HCl | 4-(nC7H15)-C6H4-CCl=O | none | 15 | 4-NC-C6H4-O-C(=O)-C6H4-nC7H15 | 87 recryst. m.p. 44-45.5° C. |

TABLE I-continued

| Ex. | ETHER | Catalyst | Acid chloride ZCCl=O | Solvent | Time (h) | Product | Yield % |
|---|---|---|---|---|---|---|---|
| 27 | 4-phenylphenyl methyl ether (Ph-C6H4-OMe) | HBGC·HCl | cinnamoyl chloride (PhCH=CH-C(=O)Cl) | none | 20 | biphenyl cinnamate (Ph-C6H4-O-C(=O)-CH=CH-Ph) | 93 recryst. |
| 28 | 2-methyl-4-methylphenyl methyl ether (Me,Me-C6H3-OMe) | HBGC·HCl | CH3(CH2)14—C(=O)Cl | none | 15 | 2,4-dimethylphenyl palmitate (Me,Me-C6H3-O-C(=O)(CH2)14CH3) | 91 recryst. |

TABLE II

| Ex. | ETHER 1 mole | Catalyst | Acid chloride | Solvent | Time (h) |
|---|---|---|---|---|---|
| 29 | MeO—C₆H₄—C(=O)—C₆H₄—OMe | HBGC 0.06 mole | PhCCl=O  3 moles | none | 20 |
| 30 | MeO—C₆H₄—C(=O)—C₆H₄—OMe | HBGC 0.06 mole | PhCCl=O  3 moles | o-DCB | 20 |
| 31 | MeO—C₆H₄—C₆H₄—OMe | HBGC 0.06 mole | PhCCl=O  5 moles | none | 20 |
| 32 | 1,3-(MeO)₂C₆H₄ | HBGC.HCl 0.05 mole | PhCCl=O  3 moles | none | 20 |

| Example | PRODUCT | Yield % |
|---|---|---|
| 29 | Ph—C(=O)O—C₆H₄—C(=O)—C₆H₄—OC(=O)—Ph | 96 recrystallization |
| 30 | Ph—C(=O)O—C₆H₄—C(=O)—C₆H₄—OC(=O)—Ph | 92 |
| 31 | Ph—C(=O)O—C₆H₄—C₆H₄—OC(=O)—Ph | 85 recrystallization |
| 32 | 1,3-(PhC(=O)O)₂C₆H₄ | 93 recrystallization |

| Ex. | ETHER 1 mole | Catalyst | Acid chloride | Solvent | Time (h) |
|---|---|---|---|---|---|
| 33 | 1,4-(MeO)₂C₆H₄ | HBGC 0.05 mole | PhCCl=O  3 moles | none | 20 |
| 34 | 2,6-dimethoxytoluene | HBGC.HCl 0.05 mole | PhCCl=O  2.5 moles | none | 20 |
| 35 | MeO—C₆H₄—O—C₆H₄—OMe | HBGC.HCl 0.055 mole | PhCCl=O  2.5 moles | none | 20 |

TABLE II-continued

| | | | | | |
|---|---|---|---|---|---|
| 36 | 3,4,5-trimethoxybenzonitrile (CN-C₆H₂(OMe)₃) | HBGC.HCl 0.05 mole | PhCCl=O  5 moles | none | 20 |

| Example | PRODUCT | Yield % |
|---|---|---|
| 33 | PhCO(O)-C₆H₄-OCPh(O) (1,4-diphenyl benzoate) | 90 recrystallization |
| 34 | 2-methyl-1,3-bis(phenylcarbonyloxy)benzene | 88 |
| 35 | PhCO(O)-C₆H₄-O-C₆H₄-OCPh(O) | 98 recrystallization |
| 36 | 4-cyano-1,2,3-tris(phenylcarbonyloxy)benzene | 94 recrystallization |

| Ex. | ETHER 1 mole | Catalyst | Acid chloride | Solvent | Time (h) |
|---|---|---|---|---|---|
| 37 | 1,2,4-trimethoxybenzene (MeO, OMe, OMe) | HBGC.HCl 0.08 mole | PhCCl=O  3.8 moles | none | 24 |
| 38 | 2,4-dimethoxytoluene (MeO, Me, OMe) | HBGC.HCl 0.05 mole | PhCCl=O  3 moles | none | 20 |
| 39 | 3,4,5-trimethoxybenzonitrile (CN, OMe, OMe, OMe) | HBGC.HCl 0.05 mole | nC₇H₁₅C—Cl =O  4.5 moles | none | 20 |
| 40 | 4,4'-dimethoxydiphenyl ether (MeO-C₆H₄-O-C₆H₄-OMe) | HBGC.HCl 0.05 mole | nC₇H₁₅C—Cl =O  2.5 moles | none | 20 |

TABLE II-continued

| | | | | | |
|---|---|---|---|---|---|
| 41 |  MeO—⬡—OMe | HBGC.HCl 0.05 mole | nC₇H₁₅C—Cl ‖ O 2.5 moles | none | 20 |

| Example | PRODUCT | Yield % |
|---|---|---|
| 37 | 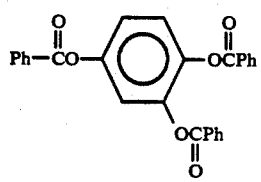 Ph—CO—⬡—OCPh, OCPh | 97 column chromatography |
| 38 | 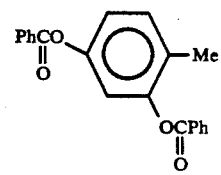 PhCO—⬡—Me, OCPh | 88 column chromatography |
| 39 | 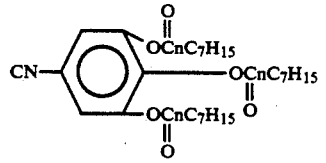 CN—⬡—OĈnC₇H₁₅ (×3) | 94 column chromatography |
| 40 | 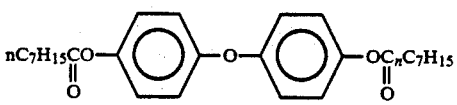 nC₇H₁₅CO—⬡—O—⬡—OCₙC₇H₁₅ | 94 recrystallization |
| 41 | 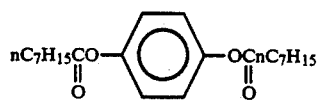 nC₇H₁₅CO—⬡—OCnC₇H₁₅ | 83 column chromatography |

| Ex. | ETHER 1 mole | Catalyst | Acid chloride | Solvent | Time (h) |
|---|---|---|---|---|---|
| 42 | 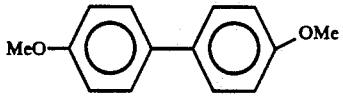 MeO—⬡—⬡—OMe | HBGC.HCl 0.06 mole | 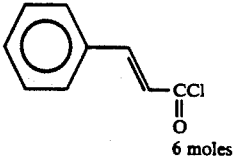 Ph-CH=CH-CCl‖O 6 moles | none | 20 |
| 43 | 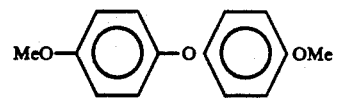 MeO—⬡—O—⬡—OMe | HBGC.HCl 0.05 mole | 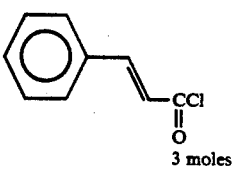 Ph-CH=CH-CCl‖O 3 moles | none | 20 |
| 44 | 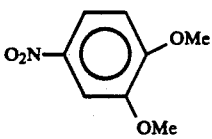 O₂N—⬡(OMe)(OMe) | HBGC.HCl 0.06 mole | PhCCl ‖ O 3 moles | none | 12 |
| 45 | 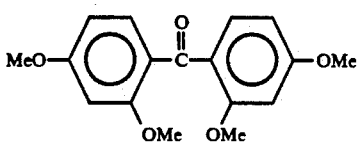 MeO—⬡—C(=O)—⬡—OMe, OMe OMe | HBGC.HCl 0.1 mole | PhCCl ‖ O 6 moles | none | 20 |

| Example | PRODUCT | Yield % |
|---|---|---|

TABLE II-continued

| Ex. | Structure | Yield % | Method |
|---|---|---|---|
| 42 | Ph-CH=CH-CO-O-C6H4-C6H4-O-CO-CH=CH-Ph | 88 | recrystallization |
| 43 | Ph-CH=CH-CO-O-C6H4-O-C6H4-O-CO-CH=CH-Ph | 96 | recrystallization |
| 44 | 4-O2N-C6H3(OC(O)Ph)2 | 97 | recrystallization |
| 45 | Benzophenone tetra-benzoate derivative | 88 | recrystallization |

TABLE III

| Ex. | BENZOATE | Hydrolysis product | Product properties | Yield % |
|---|---|---|---|---|
| 46 | PhCO-O-C6H4-CO-C6H4-O-OCPh | HO-C6H4-CO-C6H4-OH | M.p. 214–216° C. | 95 |
| 47 | PhCO-O-C6H4-C6H4-O-OCPh | HO-C6H4-C6H4-OH | M.p. 279–281° C. | 98 |
| 48 | 2-Cl-C6H4-OCPh | 2-Cl-C6H4-OH |  | 91 |
| 49 | 2,4-Me2-C6H3-OCPh | 2,4-Me2-C6H3-OH |  | 96 |
| 50 | PhCO-O-C6H4-O-C6H4-O-OCPh | HO-C6H4-O-C6H4-OH | M.p. 165–167° C. | 99 |
| 51 | Tetra-benzoate of bis(dihydroxyphenyl)methanone | Bis(2,4-dihydroxyphenyl)methanone | M.p. 197–199.5° C. | 95 |

TABLE III-continued

| Ex. | BENZOATE | Hydrolysis product | Product properties | Yield % |
|---|---|---|---|---|
| 52 | 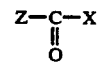 |  | M.p. 49–50.5° C. | 97 |
| 53 | 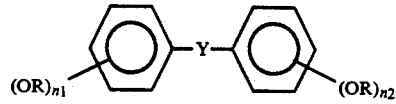 | 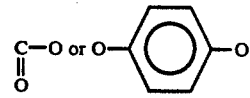 | M.p. 187–188° C. | 98 |

We claim:

1. A process for obtaining an aryl ester by O-dealkylation of an alkyl aryl ether, in which an alkyl aryl ether is reacted with an acyl halide in the presence of a catalyst chosen from a hexaalkylguanidiunium salt and a tetraalkylphosphonium salt.

2. A process as claimed in claim 1, wherein the guanidinium salt corresponds to the formula:

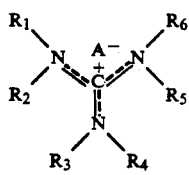

and the phosphonium salt to the formula:

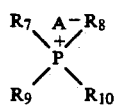

in which formulae $R_1$ to $R_{10}$ are identical or different and denote $C_1$–$C_{20}$ alkyl radicals and $A^-$ denotes an anion chosen from the group consisting of $Cl^-$, $Br^-$, $I^-$, $BF_4^-$, $CN^-$, $ClO_4^-$, $NO_3^-$, $NO_2^-$, $OCN^-$, $CH_3SO_4^-$ and $HSO_4^-$.

3. A process as claimed in claim 1, wherein the catalyst is a hexaalkylguanidinium chloride employed as such or in hydrochloride form.

4. A process as claimed in claim 3, wherein the catalyst is hexabutylguanidinium chloride or hexamethylguanidinium chloride or the hydrochloride or ether.

5. A process as claimed in claim 2, each of wherein the radicals $R_7$ to $R_{10}$ contains from 4 to 18 carbon atoms.

6. A process as claimed in claim 5, wherein the catalyst is tributylhexadecylphosphonium bromide or tetrabutylphosphonium bromide.

7. A process as claimed in claim 1, wherein the alkyl aryl ether corresponds to the formula $Ar(OR)_n$ in which:
R denotes a primary or secondary $C_1$–$C_6$ alkyl group,
n is an integer from 1 to 6 and Ar denotes:
an optionally-substituted $C_6$–$C_{14}$ aromatic radical,
the coumarinyl group or
a group of a number of phenyl radicals, optionally substituted by one or more OR groups.

8. A process as claimed in claim 1, wherein the acyl halide corresponds to the formula $$Z-C-X$$
$$\parallel$$
$$O$$

in which:
X denotes a halogen,
Z denotes
a $C_6$–$C_{10}$ aromatic radical, optionally substituted by a radical chosen from alkyl and phenoxy,
an optionally-substituted aliphatic or cycloaliphatic radical with up to 20 carbon atoms,
a phenoxy radical, said radicals optionally containing or being substituted by another $$-C-X$$
$$\parallel$$
$$O$$

group.

9. A process as claimed in claim 7, wherein $Ar(OR)_n$ is denoted by the general formula:

in which Y denotes O, $$-C-O \text{ or } O-\!\!\!\!\bigcirc\!\!\!\!-O$$
$$\parallel$$
$$O$$

or a covalent bond, and
$n_1$ and $n_2$ are identical or different integers from 1 to 3.

10. A process as claimed in claim 1, wherein the aryl ester obtained is additionally hydrolyzed in basic medium.

11. A process for obtaining an aromatic polyester as claimed in claim 8, wherein Z comprises another $$-CX$$
$$\parallel$$
$$O$$

group and n is an integer greater than or equal to 2.

12. A process as claimed in claim 1, wherein from 0.01 to 0.1 equivalent of catalyst is employed per mole of OR functional group to be cleaved.

13. A process as claimed in claim 1, wherein the reaction is performed at a temperature of between 150° C. and 220° C.

14. A process as claimed in claim 1, wherein the reaction is performed in the presence of an inert solvent.

15. A process as claimed in claim 7 wherein R denotes a methyl group.

16. A process as claimed in claim 7 wherein Ar is optionally-substituted phenyl or naphthyl wherein each optional substitutent is a member selected from the group consisting of halo, nitro, cyano, an aldehyde group, alkoxy, aryloxy, alkylaryloxy, haloalkylaryloxy, an arylketone, an alkylketone, a cycloalkylketone, aryl and optionally-substituted $C_1$–$C_{20}$ alkyl.

17. A process as claimed in claim 8 wherein X denotes Br or Cl.

18. A process as claimed in claim 8 wherein the $C_6$–$C_{10}$ aromatic radical is phenyl, the optionally-substituted aliphatic or cycloaliphatic radical has from 6 to 20 carbon atoms and is either saturated or unsaturated.

19. A process as claimed in claim 13 wherein the reaction is performed at a temperature between 180° C. and 200° C.

* * * * *